(12) United States Patent
Nuijten et al.

(10) Patent No.: US 7,601,804 B2
(45) Date of Patent: Oct. 13, 2009

(54) STREPTOCOCCUS UBERIS PROTEIN, NUCLEIC ACID SEQUENCE ENCODING THE SAME AND ITS USE IN A MASTITIS VACCINE

(75) Inventors: Petrus Johannes Maria Nuijten, Sambeek (NL); Selma Marianne Hensen, Mook (NL)

(73) Assignee: Intervet International B.V., Boxmeer (NL)

( * ) Notice: Subject to any disclaimer, the term of this patent is extended or adjusted under 35 U.S.C. 154(b) by 362 days.

(21) Appl. No.: 10/524,198

(22) PCT Filed: Aug. 6, 2003

(86) PCT No.: PCT/EP03/08704

§ 371 (c)(1), (2), (4) Date: Feb. 10, 2005

(87) PCT Pub. No.: WO2004/018683

PCT Pub. Date: Mar. 4, 2004

(65) Prior Publication Data

US 2005/0255125 A1 Nov. 17, 2005

(30) Foreign Application Priority Data

Aug. 12, 2002 (EP) .................. 02078325

(51) Int. Cl.
*C07K 1/00* (2006.01)
*G01N 33/569* (2006.01)
(52) U.S. Cl. ..................... 530/350; 435/7.34
(58) Field of Classification Search ................. 530/350; 424/244.1; 435/68.1
See application file for complete search history.

(56) References Cited

U.S. PATENT DOCUMENTS

2003/0082781 A1* 5/2003 Bolton et al. ............... 435/219

FOREIGN PATENT DOCUMENTS

| WO | WO 01 96379 A2 | 12/2001 |
| WO | WO 01 96381 A2 | 12/2001 |
| WO | WO 02 92818 A2 | 11/2002 |

OTHER PUBLICATIONS

Jayarao et al. ( Journal of Clinical Microbiology , vol. 30, No. 5, pp. 1347-1350, May 1992).*
Leigh et al. (vaccine, vol. 17, pp. 851-857, 1999).*
Burgess et al. (J of Cell Biology, 1990 vol. 111, pp. 2129 2138).*
Lazar et al (Molecular and Cellular Biology, 1988, vol. 8, pp. 1247 1252).*
Database Epofetch [Online!] (Jul. 01, 2002) Database accession No. ABN68115, XP002228319.
Database Epofetch [Online!] (Jul. 02, 2002) Database accession No. ABP27484, XP002228320.
Database Swiss-PROT [Online!] (Jun. 15, 2002) Database accession No. Q8P120, XP002228321.
Database EMBL [Online!] (Mar. 23, 2002) Database accession No. AE010036, XP002228322.
Tyler, J.W. et al.: "Immunization and immunotherapy for mastitis" Veterinary Clinics of North America (Nov. 1, 1993) V9, N3 p. 537-549, XP002095921.
Fontaine, M.C. et al.: "Immunisation of dairy cattle with recombinant *Streptococcus uberis* GapC . . . " Vaccine Butterworth Scientific. (May 22, 2002) V20 N17-18, p. 2278-2286.
Leigh, J.A. "*Streptococcus uberis*: A Permanent Barrier to the Control of Bovine Mastitis?" Veterinary Journal, (May 1999) V157, N3, p. 225-238, XP009020371.
Vermeulen, A.N. "Progress in recombinant vaccine development against coccidiosis A reveiw . . . " International J. Of Parasitology (Jul. 1998) V28, N7, P1121-1130, XP001024960.

* cited by examiner

*Primary Examiner*—Robert B. Mondesi
*Assistant Examiner*—Khatol Shahnan-Shah
(74) *Attorney, Agent, or Firm*—William M. Blackstone

(57) ABSTRACT

The present invention relates to nucleic acid sequences encoding a 22.5 kD *Streptococcus uberis* protein and to parts of such nucleic acid sequences that encode an immunogenic fragment of such proteins, and to DNA fragments, recombinant DNA molecules, live recombinant carriers and host cells comprising such nucleic acid sequences or such parts thereof. The invention also relates to a 22.5 kD *Streptococcus uberis* protein and immunogenic parts thereof encoded by such sequences. Furthermore, the present invention relates to vaccines comprising such nucleic acid sequences and parts thereof, DNA fragments, recombinant DNA molecules, live recombinant carriers and host cells comprising such nucleic acid sequences or such parts thereof, proteins or immunogenic parts thereof and antibodies against such proteins or immunogenic parts thereof. Also, the invention relates to the use of said proteins in vaccines and for the manufacture of vaccines. Moreover, the invention relates to the use of said nucleic acid sequences, proteins or antibodies for diagnostic or vaccination purposes. Finally the invention relates to diagnostic kits comprising such a nucleic acid, protein or antibodies against such protein.

3 Claims, 3 Drawing Sheets

Figure 2:
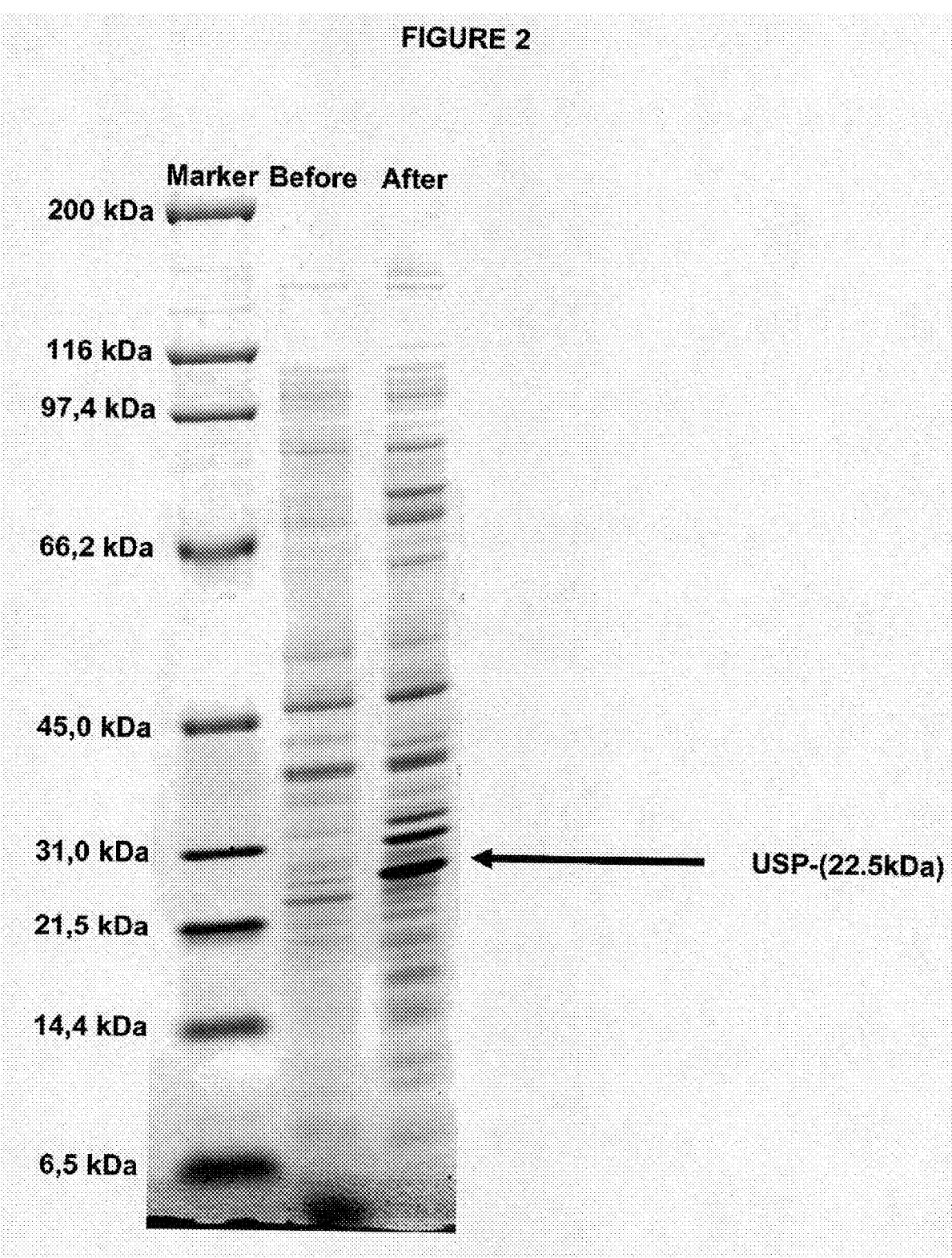

```
           BglII                    T7-promoter
          ------                --------------------
  1   atcgagatct cgatcccgcg aaattaatac gactcactat agggagacca caacgtttc
          XbaI                                                 NcoI
         -----                                                -----
 61   cctctagaaa taattttgtt taactttaag aaggagatat accatgggca gcagccatca
                                                   M  G  S  S  H  H
                                                  >>..his-MCS-his...>

EcoRV
                                                   ------
                                            NdeI           EcoRI HindIII
                                           ------         ----- -------
121   tcatcatcat cacagcagcg gcctggtgcc gcgcggcagc catatgatat cgaattcaag
       H  H  H  H  H  C  S  S  G  L  V  P  R  G  S  H  M  I  S  N  S  S
      >........his-MCS-his.................................................>

NotI      BamHI
                                                -----     -----
         KpnI  NheI  SpeI    SacI  AgeI  XhoI            SacII
        ----- ----- -----   ----- ----- -----           ------
181   cttggtaccg ctagcactag tgagctcacc ggtctcgagc ggccgcggat cccaccatca
       L  V  P  L  A  L  V  S  S  P  V  S  S  G  R  G  S  H  H  H
      >.............................his-MCS-his.................................>

ClaI
                                   -----
241   ccatcaccat caccatcacc attaatcgat gataagctgt caaacatgag cttgaagac
       H  H  H  H  H  H  H  *
      >.......his-MCS-his......>>
```

Figure 1

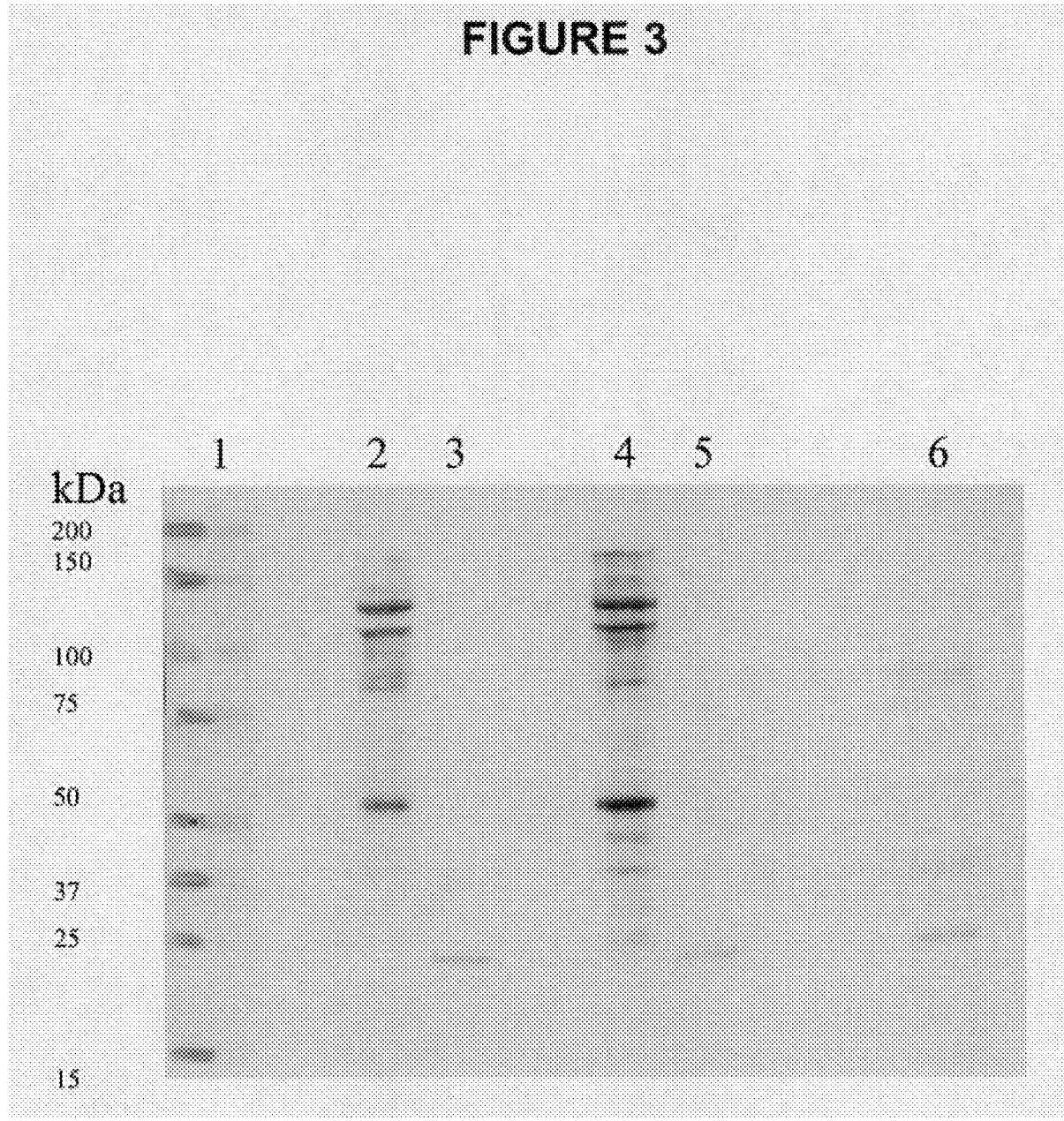

SEQUENCE LISTING

<160> NUMBER OF SEQ ID NOS: 2

<210> SEQ ID NO 1
<211> LENGTH: 603
<212> TYPE: DNA
<213> ORGANISM: Streptococcus uberis
<220> FEATURE:
<221> NAME/KEY: CDS
<222> LOCATION: (1)..(600)
<223> OTHER INFORMATION:

<400> SEQUENCE: 1

```
atg ttt aaa ttt tta aag cgt gtt gtt ttt cta gct ttt ctg att ttt      48
Met Phe Lys Phe Leu Lys Arg Val Val Phe Leu Ala Phe Leu Ile Phe
1               5                   10                  15 tgt ttt tat caa gct tat ata aca cat caa aat gta caa aat gtc atg      96
Cys Phe Tyr Gln Ala Tyr Ile Thr His Gln Asn Val Gln Asn Val Met
                20                  25                  30 caa tac aaa cca atg gtt gaa aaa acc ttg gct gaa aat gat acg act     144
Gln Tyr Lys Pro Met Val Glu Lys Thr Leu Ala Glu Asn Asp Thr Thr
            35                  40                  45 gcc aat gtc aat tta gtt tta gca atg atc tac aca gaa aca aaa ggt     192
Ala Asn Val Asn Leu Val Leu Ala Met Ile Tyr Thr Glu Thr Lys Gly
        50                  55                  60 ggt cag gca gat gtc atg caa tct agc gaa agt agt agt ggt gtg act     240
Gly Gln Ala Asp Val Met Gln Ser Ser Glu Ser Ser Ser Gly Val Thr
65                  70                  75                  80 aac tca att acc gac agt caa tct agt att caa cac ggt gtc aaa ctc     288
Asn Ser Ile Thr Asp Ser Gln Ser Ser Ile Gln His Gly Val Lys Leu
                85                  90                  95 ttg tct gag aat ttg act tta gct gag aaa gct gga gta gac tct tgg     336
Leu Ser Glu Asn Leu Thr Leu Ala Glu Lys Ala Gly Val Asp Ser Trp
            100                 105                 110 act gca gta caa gct tac aat ttt gga aca gct tac att gat tat gtg     384
Thr Ala Val Gln Ala Tyr Asn Phe Gly Thr Ala Tyr Ile Asp Tyr Val
        115                 120                 125 gca aaa aat ggt ggt gac aac act atc tct ttg gct agt cat tat tct     432
Ala Lys Asn Gly Gly Asp Asn Thr Ile Ser Leu Ala Ser His Tyr Ser
    130                 135                 140 aaa agt gtt gta gct cca agt tta ggg aat aag gat gga aaa atg tat     480
Lys Ser Val Val Ala Pro Ser Leu Gly Asn Lys Asp Gly Lys Met Tyr
145                 150                 155                 160 tta tat tac cat cca att gcc ctc ctc tat ggc ggt aaa ctt tat caa     528
Leu Tyr Tyr His Pro Ile Ala Leu Leu Tyr Gly Gly Lys Leu Tyr Gln
                165                 170                 175 aat ggt ggt aat att tat tat tca cga gaa gtt cat ttt aat tat tac     576
Asn Gly Gly Asn Ile Tyr Tyr Ser Arg Glu Val His Phe Asn Tyr Tyr
```

-continued

```
                180                 185                 190
ctc ata caa tta tta tct aaa ttt taa                                    603
Leu Ile Gln Leu Leu Ser Lys Phe
        195                 200

<210> SEQ ID NO 2
<211> LENGTH: 200
<212> TYPE: PRT
<213> ORGANISM: Streptococcus uberis

<400> SEQUENCE: 2

Met Phe Lys Phe Leu Lys Arg Val Val Phe Leu Ala Phe Leu Ile Phe
1               5                   10                  15

Cys Phe Tyr Gln Ala Tyr Ile Thr His Gln Asn Val Gln Asn Val Met
            20                  25                  30

Gln Tyr Lys Pro Met Val Glu Lys Thr Leu Ala Glu Asn Asp Thr Thr
        35                  40                  45

Ala Asn Val Asn Leu Val Leu Ala Met Ile Tyr Thr Glu Thr Lys Gly
    50                  55                  60

Gly Gln Ala Asp Val Met Gln Ser Ser Glu Ser Ser Ser Gly Val Thr
65                  70                  75                  80

Asn Ser Ile Thr Asp Ser Gln Ser Ser Ile Gln His Gly Val Lys Leu
                85                  90                  95

Leu Ser Glu Asn Leu Thr Leu Ala Glu Lys Ala Gly Val Asp Ser Trp
            100                 105                 110

Thr Ala Val Gln Ala Tyr Asn Phe Gly Thr Ala Tyr Ile Asp Tyr Val
        115                 120                 125

Ala Lys Asn Gly Gly Asp Asn Thr Ile Ser Leu Ala Ser His Tyr Ser
    130                 135                 140

Lys Ser Val Val Ala Pro Ser Leu Gly Asn Lys Asp Gly Lys Met Tyr
145                 150                 155                 160

Leu Tyr Tyr His Pro Ile Ala Leu Leu Tyr Gly Gly Lys Leu Tyr Gln
                165                 170                 175

Asn Gly Gly Asn Ile Tyr Tyr Ser Arg Glu Val His Phe Asn Tyr Tyr
            180                 185                 190

Leu Ile Gln Leu Leu Ser Lys Phe
        195                 200
```

STREPTOCOCCUS UBERIS PROTEIN, NUCLEIC ACID SEQUENCE ENCODING THE SAME AND ITS USE IN A MASTITIS VACCINE

CROSS REFERENCE TO RELATED APPLICATIONS

This application is a §371 application depending from PCT/EP2003/008704 filed on Aug. 6, 2003.

REFERENCE TO SEQUENCE LISTING

The material saved as "text document" under the file name "SubstituteSequenceListing" created on Feb. 4, 2008 is hereby incorporated by reference.

The present invention relates to nucleic acid sequences encoding a *Streptococcus uberis* protein and to parts of such nucleic acid sequences that encode an immunogenic fragment of such proteins, and to DNA fragments, recombinant DNA molecules, live recombinant carriers and host cells comprising such nucleic acid sequences or such parts thereof. The invention also relates to a *Streptococcus uberis* protein and immunogenic parts thereof encoded by such sequences. Furthermore, the present invention relates to vaccines comprising such nucleic acid sequences and parts thereof, DNA fragments, recombinant DNA molecules, live recombinant carriers and host cells comprising such nucleic add sequences or such parts thereof, proteins or immunogenic parts thereof and antibodies against such proteins or immunogenic parts thereof. Also, the invention relates to the use of said proteins in vaccines and for the manufacture of vaccines. Moreover, the invention relates to the use of said nucleic acid sequences, proteins or antibodies for diagnostic or vaccination purposes. Finally the invention relates to diagnostic kits comprising such a nucleic acid, protein or antibodies against such protein.

Mastitis in cows is an inflammation of the mammary gland, that usually occurs after intramammary infection. Mastitis is primarily caused by bacteria, although mycoplasmal, mycotic and algal infections are known to be able to cause mastiffs as well.

Mastitis is the most costly disease in diary cattle. The amount of money lost yearly in the USA only, exceeds $2.000.000.000. The combined losses due to discarded milk and decreased milk production is responsible for about 75% of the costs of mastitis, whereas loss of animals, labor costs and vet costs are responsible for about 25% of the total costs.

In principle, two types of mastitis are distinguished: contagious mastitis and environmental mastitis. Contagious mastitis is the type of mastitis that spreads from one cow to the other. The most important pathogens involved in cow-to-cow mastitis are *Staphylococcus aureus, Streptococcus agalactiae* and Mycoplasma.

Environmental mastitis is the type of mastitis caused by pathogenic microorganisms found in the environment. The most common causes of environment-to-cow mastitis are on the one hand coliform bacteria such as *E. coli, Enterobacter, Klebsiella* and *Citrobacter*, and on the other hand *Streptococcal* species such as *Streptococcus uberis* and *Streptococcus dysgalactiae*.

It is clear that mastitis is a multifactor disease and therefore several routes have to be followed in order to prevent or control mastitis. One of these routes is aiming at a microbiologically clean environment, which is highly desirable but practically impossible. Another one is the use of pharmaceutical components, such as the extensive use of antibiotics, more precisely antibacterials which nowadays is a very common therapy in the treatment of mastitis.

Still another one is undoubtedly vaccination against the various pathogens involved in mastitis. It is thus clear that, especially where there is an increasing reluctance against the use of antibiotics, there is a need for new and effective vaccines, especially vaccines that provide broad protection.

It is an objective of the present invention to provide a novel vaccine component for combating mastitis infection.

It was now surprisingly found that a novel *Streptococcus uberis* protein exists, that can be used as a valuable vaccine component, either alone or in combination with other vaccine components.

The gene encoding this protein has now been cloned and sequenced and its sequence is depicted in SEQ ID NO: 1. The gene encodes a protein of 200 amino acids (as depicted in SEQ ID NO: 2) with a molecular mass of 22.5 kD.

It is well-known in the art, that many different nucleic acid sequences can encode one and the same protein. This phenomenon is commonly known as wobble in the second and especially the third base of each triplet encoding an amino acid. This phenomenon can result in a heterology for two nucleic acid sequences still encoding the same protein. Therefore, two nucleic acid sequences having a sequence homology as low as 70% can still encode one and the same protein.

Thus, one embodiment relates to a nucleic acid sequence encoding a 22.5 kD *Streptococcus uberis* protein or a part of said nucleic acid sequence that encodes an immunogenic fragment of said protein wherein said nucleic acid sequence or said part thereof has at least 85% homology with the nucleic acid sequence of the 22.5 kD *Streptococcus uberis* protein gene as depicted in SEQ ID NO: 1.

The concept of immunogenic fragment is defined below. The length of a nucleic acid sequence encoding an immunogenic fragment is usually at least 21 nucleotides, but preferably 24, 27, 30, 33 or even 36 nucleotides.

The molecular weight of 22.5 kD is determined in gel electrophoresis on a polyacryl amide gel. Due to slight variability of molecular weight determination frequently encountered in the art, the molecular weight can vary between 19.5 and 25.5 kD. Therefore the molecular weight of the proteins according to the invention should be interpreted as to be 22.5+/−3 kD.

Preferably, a nucleic acid sequence according to the invention encoding this 22.5 *Streptococcus uberis* protein or a part of that nucleic acid sequence that encodes an immunogenic fragment of that protein has at least 90%, preferably 93%, more preferably 95% homology with the nucleic acid sequence of the *Streptococcus uberis* protein gene as depicted in SEQ ID NO: 1.

Even more preferred is a homology level of 98%, 99% or even 100%.

The level of nucleotide homology can be determined with the computer program "BLAST 2 SEQUENCES" by selecting sub-program: "BLASTP." A reference for this program is Tatiana A. Tatusova, Thomas L. Madden FEMS Microbial. Letters 174: 247-250 (1999). Parameters used are the default parameters: Reward for a match: +1. Penalty for a mismatch: −2. Open gap: 5.

Extension gap: 2.

Gap x_{dropoff}: 50.

Nucleotide sequences that are complementary to the sequence depicted in SEQ ID NO 1 or nucleotide sequences that comprise tandem arrays of the sequences according to the invention are also within the scope of the invention.

Since the present invention discloses nucleic acid sequences encoding a novel 22.5 kD *Streptococcus uberis* protein, it is now for the first time possible to obtain this protein in sufficient quantities. This can e.g. be done by using expression systems to express the whole or parts of the gene encoding the protein or an immunogenic fragment thereof.

Therefore, in a more preferred form of this embodiment, the invention relates to DNA fragments comprising a nucleic acid sequence according to the invention. A DNA fragment is a stretch of nucleotides that functions as a carrier for a nucleic acid sequence according to the invention. Such DNA fragments can e.g. be plasmids, into which a nucleic acid sequence according to the invention is cloned. Such DNA fragments are e.g. useful for enhancing the amount of DNA for use as a primer and for expression of a nucleic acid sequence according to the invention, as described below.

An essential requirement for the expression of the nucleic acid sequence is an adequate promoter functionally linked to the nucleic acid sequence, so that the nucleic acid sequence is under the control of the promoter. It is obvious to those skilled in the art that the choice of a promoter extends to any eukaryotic, prokaryotic or viral promoter capable of directing gene transcription in cells used as host cells for protein expression.

Therefore, an even more preferred form of this embodiment relates to a recombinant DNA molecule comprising a DNA fragment and/or a nucleic acid sequence according to the invention wherein the nucleic acid sequence according to the invention is placed under the control of a functionally linked promoter. This can be obtained by means of e.g. standard molecular biology techniques. (Maniatis/Sambrook (Sambrook, J. Molecular cloning: a laboratory manual, 1989. ISBN 0-87969-309-6). Functionally linked promoters are promoters that are capable of controlling the transcription of the nucleic acid sequences to which they are linked.

Such a promoter can be the native promoter of the novel gene or another promoter of *Streptococcus uberis*, provided that that promoter is functional in the cell used for expression. It can also be a heterologous promoter. When the host cells are bacteria, useful expression control sequences which may be used include the Trp promoter and operator (Goeddel, et al., Nucl. Acids Res., 8, 4057, 1980); the lac promoter and operator (Chang, et al., Nature, 275, 615, 1978); the outer membrane protein promoter (Nakamura, K. and Inouge, M., EMBO J., 1, 771-775, 1982); the bacteriophage lambda promoters and operators (Remaut, E. et al., Nucl. Adds Res., 11, 4677-4688, 1983); the α-amylase (*B. subtillis*) promoter and operator, termination sequences and other expression enhancement and control sequences compatible with the selected host cell.

When the host cell is yeast, useful expression control sequences include, e.g., α-mating factor. For insect cells the polyhedrin or p10 promoters of baculoviruses can be used (Smith, G. E. et al., Mol. Cell. Biol. 3, 2156-65, 1983). When the host cell is of vertebrate origin illustrative useful expression control sequences include the (human) cytomegalovirus immediate early promoter (Seed, B. et al., Nature 329 840-842, 1987; Fynan, E. F. et al., PNAS 90, 11478-11482, 1993; Ulmer, J. B. et al., Science 259, 1745-1748, 1993), Rous sarcoma virus LTR (RSV, Gorman, C. M. et al., PNAS 79, 6777-6781, 1982; Fynan et al., supra; Ulmer et al., supra), the MPSV LTR (Stacey et al., J. Virology 50, 725-732, 1984). SV40 immediate early promoter (Sprague J. et al., J. Virology 45, 773, 1983), the SV-40 promoter (Berman, P. W. et al., Science, 222, 524-527, 1983), the metallothionein promoter (Brinster, R. L. et al., Nature 296, 39-42, 1982), the heat shock promoter (Voellmy et al., Proc. Natl. Acad. Sci. USA, 82, 4949-53, 1985), the major late promoter of Ad2 and the β-actin promoter (Tang et al., Nature 356, 152-154, 1992). The regulatory sequences may also include terminator and poly-adenylation sequences. Amongst the sequences that can be used are the well known bovine growth hormone poly-adenylation sequence, the SV40 poly-adenylation sequence, the human cytomegalovirus (hCMV) terminator and poly-adenylation sequences.

Bacterial, yeast, fungal, insect and vertebrate cell expression systems are very frequently used systems. Such systems are well-known in the art and generally available, e.g. commercially through Clontech Laboratories, Inc. 4030 Fabian Way, Palo Alto, Calif. 94303-4607, USA. Next to these expression systems, parasite-based expression systems are attractive expression systems. Such systems are e.g. described in the French Patent Application with Publication number 2 714 074, and in US NTIS Publication No U.S. Ser. No. 08/1043109 (Hoffman, S. and Rogers, W.: Public. Date 1 Dec. 1993).

A still even more preferred form of this embodiment of the invention relates to Live Recombinant Carriers (LRCs) comprising a nucleic acid sequence encoding a 22.5 kD *Streptococcus uberis* protein or an immunogenic fragment thereof according to the invention, a DNA fragment according to the invention or a recombinant DNA molecule according to the invention. These LRCs are micro-organisms or viruses in which additional genetic information, in this case a nucleic acid sequence encoding the 22.5 kD *Streptococcus uberis* protein or an immunogenic fragment thereof according to the invention has been cloned. Cows infected with such LRCs will produce an immunological response not only against the immunogens of the carrier, but also against the immunogenic parts of the protein(s) for which the genetic code is additionally cloned into the LRC, e.g. the novel 22.5 kD *Streptococcus uberis* protein gene according to the invention.

As an example of bacterial LRCs, attenuated *Salmonella* strains known in the art can very attractively be used.

Also, live recombinant carrier parasites have i.a. been described by Vermeulen, A. N. (Int. Journ. Parasitol. 28: 1121-1130 (1998)).

Furthermore, LRC viruses may be used as a way of transporting the nucleic acid sequence into a target cell. Live recombinant carrier viruses are also called vector viruses. Viruses often used as vectors are Vaccinia viruses (Panicali et al; Proc. Natl. Acad. Sci. USA, 79: 4927 (1982), Herpesviruses (E.P.A. 0473210A2), and Retroviruses (Vaterio, D. et al; in Baum, S. J., Dicke, K. A., Lotzova, E. and Pluznik, D. H. (Eds.), Experimental Haematology today—1988. Springer Verlag, New York: pp. 92-99 (1989)).

The technique of in vivo homologous recombination, well-known in the art, can be used to introduce a recombinant nucleic acid sequence into the genome of a bacterium, parasite or virus of choice, capable of inducing expression of the inserted nucleic add sequence according to the invention in the host animal.

Finally another form of this embodiment of the invention relates to a host cell comprising a nucleic acid sequence encoding a protein according to the invention, a DNA fragment comprising such a nucleic acid sequence or a recombinant DNA molecule comprising such a nucleic acid sequence under the control of a functionally linked promoter. This form also relates to a host cell containing a live recombinant carrier comprising a nucleic acid molecule encoding a 22.5 kD *Streptococcus uberis* protein or an immunogenic fragment thereof according to the invention.

A host cell may be a cell of bacterial origin, e.g. *Escherichia coli, Bacillus subtilis* and *Lactobacillus* species, in combination with bacteria-based plasmids as pBR322, or bacterial expression vectors as the pEX-, pET-, pGEX-series, or with bacteriophages. The host cell may also be of eukaryotic origin, e.g. yeast-cells in combination with yeast-specific vector molecules, or higher eukaryotic cells like insect cells (Luckow et al; Bio-technology 6: 47-55 (1988)) in combination with vectors or recombinant baculoviruses, plant cells in combination with e.g. Ti-plasmid based vectors or plant viral vectors (Barton, K. A. et al; Cell 32: 1033 (1983), mammalian cells like Hela cells, Chinese Hamster Ovary cells (CHO) or Crandell Feline Kidney-cells, also with appropriate vectors or recombinant viruses.

Another embodiment of the invention relates to the novel 22.5 kD *Streptococcus uberis* protein and to immunogenic fragments thereof according to the invention.

The concept of immunogenic fragments will be defined below.

One form of this embodiment relates to a 22.5 kD *Streptococcus uberis* protein and to immunogenic fragments thereof having a length of at least 33 amino acids, wherein the protein or immunogenic fragments have a sequence homology of at least 93%, preferably however 94%, more preferably 95% or even 96% homology, in that order or preference, to the amino acid sequence as depicted in SEQ ID NO: 2.

Even more preferred is a homology level of 97%, 98%, 99% or even 100% in that order of preference.

The immunogenic fragments of the *Streptococcus uberis* protein according to the invention preferably have a length of at least 33, more preferably 35, 38, 41, 45 or even 50 amino acids, in that order of preference.

A more preferred form of this embodiment relates to a 22.5 kD *Streptococcus uberis* protein and immunogenic fragments of said protein, encoded by a nucleic acid sequence according to the present invention.

The level of protein homology can be determined with the computer program "BLAST 2 SEQUENCES" by selecting sub-program: "BLASTP."

A reference for this program is Tatiana A. Tatusova, Thomas L. Madden FEMS Microbiol. Letters 174: 247-250 (1999). Matrix used: "blosum62". Parameters used are the default parameters: Open gap: 11. Extension gap: 1. Gap $x_{\_dropoff}$: 50.

It will be understood that, for the particular proteins embraced herein, natural variations can exist between individual *Streptococcus uberis* strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Other amino add substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science, 227, 1435-1441, 1985) and determining the functional similarity between homologous proteins. Such amino acid substitutions of the exemplary embodiments of this invention, as well as variations having deletions and/or insertions are within the scope of the invention as long as the resulting proteins retain their immune reactivity. This explains why *Streptococcus uberis* proteins according to the invention, when isolated from different field isolates, may have homology levels of about 70%, while still representing the same protein with the same immunological characteristics. Those variations in the amino acid sequence of a certain protein according to the invention that still provide a protein capable of inducing an immune response against infection with *Streptococcus uberis* or at least against the clinical manifestations of the infection are considered as "not essentially influencing the immunogenicity".

When a protein is used for e.g. vaccination purposes or for raising antibodies, it is however not necessary to use the whole protein. It is also possible to use a fragment of that protein that is capable, as such or coupled to a carrier such as e.g. KLH, of inducing an immune response against that protein, a so-called immunogenic fragment. An "immunogenic fragment" is understood to be a fragment of the full-length protein that still has retained its capability to induce an immune response in a vertebrate host, e.g. comprises a B- or T-cell epitope. Shortly, an immunogenic fragment is a fragment that is capable of inducing an antigenic response against the 22.5 kD *Streptococcus uberis* protein according to the invention. At this moment, a variety of techniques is available to easily identify DNA fragments encoding antigenic fragments (determinants). The method described by Geysen et al (Patent Application WO 84/03564, Patent Application WO 86/06487, U.S. Pat. No. 4,833,092, Proc. Natl Acad. Sci. 81: 3998-4002 (1984), J. Imm. Meth. 102, 259-274 (1987), the so-called PEPSCAN method is an easy to perform, quick and well-established method for the detection of epitopes; the immunologically important regions of the protein. The method is used world-wide and as such well-known to man skilled in the art. This (empirical) method is especially suitable for the detection of B-cell epitopes. Also, given the sequence of the gene encoding any protein, computer algorithms are able to designate specific protein fragments as the immunologically important epitopes on the basis of their sequential and/or structural agreement with epitopes that are now known. The determination of these regions is based on a combination of the hydrophilicity criteria according to Hopp and Woods (Proc. Natl. Aced. Sci. 78: 38248-3828 (1981)), and the secondary structure aspects according to Chou and Fasman (Advances in Enzymology 47: 45-148 (1987) and U.S. Pat. No. 4,554,101). T-cell epitopes can likewise be predicted from the sequence by computer with the aid of Berzofsky's amphiphilicity criterion (Science 235, 1059-1062 (1987) and U.S. patent application Ser. No. 07/005, 885). A condensed overview is found in: Shan Lu on common principles: Tibtech 9: 238-242 (1991), Good et al on Malaria epitopes; Science 235: 1059-1062 (1987), Lu for a review; Vaccine 10: 3-7 (1992), Berzofsky for HIV-epitopes; The FASEB Journal 5:2412-2418 (1991). An immunogenic fragment usually has a minimal length of 6, more commonly 8 amino acids, preferably more then 8, such as 9, 10, 12, 15 or even 20 or more amino acids. The nucleic acid sequences encoding such a fragment therefore have a length of at least 18, more commonly 24 and preferably 27, 30, 36, 45 or even 60 nucleic acids.

Therefore, one form of still another embodiment of the invention relates to vaccines for combating *Streptococcus uberis* infection, that comprise a 22.5 kD *Streptococcus uberis* protein or immunogenic fragments thereof, according to the invention as described above together with a pharmaceutically acceptable carrier.

Still another embodiment of the present invention relates to the 22.5 kD *Streptococcus uberis* protein according to the invention or immunogenic fragments thereof for use in a vaccine.

Again another embodiment of the present invention relates to the use of a 22.5 kD *Streptococcus uberis* protein, or an immunogenic fragment of that protein having a length of at least 6 amino acids, wherein that protein or immunogenic fragment thereof has an amino acid sequence homology of at least 70%, preferably 80%, more preferably 85% with the amino acid sequence as depicted in SEQ ID NO: 2 for the manufacturing of a vaccine for combating *Streptococcus uberis* infection.

Even more preferred is a sequence homology of 90%, 95%, 97%, 98%, 99% or even 100% in that order of preference.

Still another embodiment of the present invention relates to the use of a nucleic acid sequence, a DNA fragment, a recombinant DNA molecule, a live recombinant carrier, a host cell or a protein or an immunogenic fragment thereof according to the invention for the manufacturing of a vaccine, more specifically a vaccine for combating *Streptococcus uberis* infection.

One way of making a vaccine according to the invention is by growing the bacteria, followed by biochemical purification of the 22.5 kD *Streptococcus uberis* protein or immunogenic fragments thereof, from the bacterium. This is however a very time-consuming way of making the vaccine.

It is therefore much more convenient to use the expression products of the gene encoding a 22.5 kD *Streptococcus uberis* protein or immunogenic fragments thereof in vaccines. This is possible for the first time now because the nucleic acid sequence of the gene encoding a 22.5 kD protein is provided in the present invention.

Vaccines based upon the expression products of these genes can easily be made by admixing the protein according to the invention or immunogenic fragments thereof according to the invention with a pharmaceutically acceptable carrier as described below.

Alternatively, a vaccine according to the invention can comprise live recombinant carriers as described above, capable of expressing the protein according to the invention or immunogenic fragments thereof. Such vaccines, e.g. based upon a *Salmonella* carrier or a viral carrier e.g. a Herpesvirus vector have the advantage over subunit vaccines that they better mimic the natural way of infection of *Streptococcus uberis*. Moreover, their self-propagation is an advantage since only low amounts of the recombinant carrier are necessary for immunization.

Vaccines can also be based upon host cells as described above, that comprise the protein or immunogenic fragments thereof according to the invention.

All vaccines described above contribute to active vaccination, i.e. they trigger the host's defense system.

Alternatively, antibodies can be raised in e.g. rabbits or can be obtained from antibody-producing cell lines as described below. Such antibodies can then be administered to the cow. This method of vaccination, passive vaccination, is the vaccination of choice when an animal is already infected, and there is no time to allow the natural immune response to be triggered. It is also the preferred method for vaccinating animals that are prone to sudden high infection pressure. The administered antibodies against the protein according to the invention or immunogenic fragments thereof can in these cases interfere with *Streptococcus uberis*. This has the advantage that it decreases or stops *Streptococcus uberis* multiplication.

Therefore, one other form of this embodiment of the invention relates to a vaccine for combating *Streptococcus uberis* infection that comprises antibodies against a *Streptococcus uberis* protein according to the invention or an immunogenic fragment of that protein, and a pharmaceutically acceptable carrier.

Still another embodiment of this invention relates to antibodies against a *Streptococcus uberis* protein according to the invention or an immunogenic fragment of that protein.

Methods for large-scale production of antibodies according to the invention are also known in the art. Such methods rely on the cloning of (fragments of) the genetic information encoding the protein according to the invention in a filamentous phage for phage display. Such techniques are described i.a. in review papers by Cortese, R. et al., (1994) in Trends Boitechn. 12: 262-267., by Clackson, T. & Wells, J. A. (1994) in Trends Biotechn. 12: 173-183, by Marks, J. D. et al., (1992) in J. Biol. Chem. 267: 16007 16010, by Winter, G. et al., (1994) in Annu. Rev. Immunol. 12: 433-455, and by Little, M. et al., (1994) Biotechn. Adv. 12: 539-555. The phages are subsequently used to screen camelid expression libraries expressing camelid heavy chain antibodies. (Muyldermans, S. and Lauwereys, M., Journ. Molec. Recogn. 12:131-140 (1999) and Chabroudi, M.A. et al., FEBS Letters 414: 512-526 (1997)). Cells from the library that express the desired antibodies can be replicated and subsequently be used for large scale expression of antibodies.

Still another embodiment relates to a method for the preparation of a vaccine according to the invention that comprises the admixing of antibodies according to the invention and a pharmaceutically acceptable carrier.

An alternative and efficient way of vaccination is direct vaccination with DNA encoding the relevant antigen. Direct vaccination with DNA encoding proteins has been successful for many different proteins. (As reviewed in e.g. Donnelly et al., The Immunologist 2: 20-26 (1993)). This way of vaccination is also attractive for the vaccination of cows against *Streptococcus uberis* infection. Therefore, still other forms of this embodiment of the invention relate to vaccines comprising nucleic acid sequences encoding a protein according to the invention or immunogenic fragments thereof, comprising DNA fragments that comprise such nucleic acid sequences or comprising recombinant DNA molecules according to the invention, and a pharmaceutically acceptable carrier.

Examples of DNA plasmids that are suitable for use in a DNA vaccine according to the invention are conventional cloning or expression plasmids for bacterial, eukaryotic and yeast host cells, many of said plasmids being commercially available. Well-known examples of such plasmids are pBR322 and pcDNA3 (Invitrogen). The DNA fragments or recombinant DNA molecules according to the invention should be able to induce protein expression of the nucleotide sequences. The DNA fragments or recombinant DNA molecules may comprise one or more nucleotide sequences according to the invention. In addition, the DNA fragments or recombinant DNA molecules may comprise other nucleotide sequences such as the immune-stimulating oligonucleotides having unmethylated CpG di-nucleotides, or nucleotide sequences that code for other antigenic proteins or adjuvating cytokines.

The nucleotide sequence according to the present invention or the DNA plasmid comprising a nucleotide sequence according to the present invention, preferably operably linked to a transcriptional regulatory sequence, to be used in the vaccine according to the invention can be naked or can be packaged in a delivery system. Suitable delivery systems are lipid vesicles, iscoms, dendromers, niosomes, polysaccharide matrices and the like, (see further below) all well-known in the art. Also very suitable as delivery system are attenuated live bacteria such as *Salmonella* species, and attenuated live viruses such as Herpesvirus vectors, as mentioned above.

Still other forms of this embodiment relate to vaccines comprising recombinant DNA molecules according to the invention.

DNA vaccines can e.g. easily be administered through intradermal application such as by using a needle-less injector. This way of administration delivers the DNA directly into the cells of the animal to be vaccinated. Amounts of DNA in the range between 10 pg and 1000 μg provide good results. Preferably, amounts in the microgram range between 1 and 100 μg are used.

In a further embodiment, the vaccine according to the present invention additionally comprises one or more antigens derived from cow pathogenic organisms and viruses, antibodies against those antigens or genetic information encoding such antigens and/or a pharmaceutical component such as an antibiotic.

Of course, such antigens, antibodies against such antigens, or genetic information can be of *Streptococcus uberis* origin, such as e.g. another *Streptococcus uberis* antigen. It can also be an antigen, antibodies or genetic information selected from another cow pathogenic organism or virus. Such organisms and viruses are preferably selected from the group of Bovine Herpesvirus, bovine Viral Diarrhoea virus, Parainfluenza type 3 virus, Bovine Paramyxovirus, Foot and Mouth Disease virus, *Pasteurella haemolytica*, Bovine Respiratory Syncytial Virus, *Theileria* sp., *Babesla* sp., *Trypanosoma* species, *Anaplasma* sp., *Neospora caninum, Staphylococcus aureus, Streptococcus agalactiae*, Mycoplasma, *E. coli, Enterobacter, Klebsiella, Citrobacter* and *Streptococcus dysgalactiae*.

Vaccines based upon the 22.5 kD *Streptococcus uberis* protein are also very suitable as marker vaccines. A marker vaccine is a vaccine that allows to discriminate between vaccinated and field-infected cows e.g. on the basis of a characteristic antibody panel, different from the antibody panel induced by wild type infection. A different antibody panel is induced e.g. when an immunogenic protein present on a wild type bacterium is not present in a vaccine: the host will then not make antibodies against that protein after vaccination. Thus, a vaccine based upon the 22.5 kD *Streptococcus uberis* protein according to the invention would only induce antibodies against the 22.5 kD protein, whereas a vaccine based upon a live wild-type, live attenuated or inactivated whole *Streptococcus uberis* would induce antibodies against all or most of the bacterial proteins.

A simple ELISA test, having wells comprising e.g. another, i.e. non-22.5 kD *Streptococcus uberis* protein and wells comprising only purified 22.5 kD *Streptococcus uberis* protein suffices to test serum from cows and to tell if the cows are either vaccinated with the 22.5 kD protein vaccine or suffered from *Streptococcus uberis* field infection.

All vaccines according to the present invention comprise a pharmaceutically acceptable carrier. A pharmaceutically acceptable carrier can be e.g. sterile water or a sterile physiological salt solution. In a more complex form the carrier can e.g. be a buffer.

Methods for the preparation of a vaccine comprise the admixing of a protein or an immunogenic fragment thereof, according to the invention and/or antibodies against that protein or an immunogenic fragment thereof, and/or a nucleic acid sequence and/or a DNA fragment, a recombinant DNA molecule, a live recombinant carrier or host cell according to the invention, and a pharmaceutically acceptable carrier.

Vaccines according to the present invention may in a preferred presentation also contain an immunostimulatory substance, a so-called adjuvant. Adjuvants in general comprise substances that boost the immune response of the host in a non-specific manner. A number of different adjuvants are known in the art. Examples of adjuvants frequently used in cow vaccines are muramyldipeptides, lipopolysaccharides, several glucans and glycans and CARBOPOL® (an acrylic homopolymer). The vaccine may also comprise a so-called "vehicle". A vehicle is a compound to which the protein adheres, without being covalently bound to it. Such vehicles are i.a. bio-microcapsules, micro-alginates, liposomes and macrosols, all known in the art.

A special form of such a vehicle, in which the antigen is partially embedded in the vehicle, is the so-called ISCOM (EP 109.942, EP 180.564, EP 242.3 80) In addition, the vaccine may comprise one or more suitable surface-active compounds or emulsifiers, e.g. SPAN™ or TWEEN™.

Often, the vaccine is mixed with stabilisers, e.g. to protect degradation-prone proteins from being degraded, to enhance the shelf-life of the vaccine, or to improve freeze-drying efficiency. Useful stabilisers are i.e. SPGA (Bovamik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent. It goes without saying, that other ways of adjuvating, adding vehicle compounds or diluents, emulsifying or stabilising a protein are also embodied in the present invention.

Vaccines according to the invention that are based upon the protein according to the invention or immunogenic fragments thereof can very suitably be administered in amounts ranging between 1 and 100 micrograms of protein per animal, although smaller doses can in principle be used. A dose exceeding 100 micrograms will, although immunologically very suitable, be less attractive for commercial reasons.

Vaccines based upon live attenuated recombinant carriers, such as the LRC-viruses and bacteria described above can be administered in much lower doses, because they multiply themselves during the infection. Therefore, very suitable amounts would range between $10^3$ and $10^9$ CFU/PFU for both bacteria and viruses.

Vaccines according to the invention can be administered e.g. intradermally, subcutaneously, intramuscularly, intraperitoneally, intravenously, or at mucosal surfaces such as orally or intranasally.

For efficient protection against disease, a quick and correct diagnosis of *Streptococcus uberis* infection is important. Therefore it is another objective of this invention to provide diagnostic tools suitable for the detection of *Streptococcus uberis* infection.

The nucleic acid sequences, the proteins and the antibodies according to the invention are also suitable for use in diagnostics.

Therefore, another embodiment of the invention relates to nucleic acid sequences, proteins and antibodies according to the invention for use in diagnostics.

The nucleic add sequences or fragments thereof according to the invention can be used to detect the presence of *Streptococcus uberis* in cows. A sample taken from cows infected with *Streptococcus uberis* will comprise nucleic acid material derived from said bacterium, including nucleic acid sequences encoding for the protein according to the invention. These nucleic acid sequences will hybridize with a nucleic acid sequence according to the invention. Suitable methods for the detection of nucleic acid sequences that are reactive with the nucleic acid sequences of the present invention include hybridization techniques including but not limited to PCR techniques and NASBA techniques. Thus the nucleic acid sequences according to the invention, in particular the sequence depicted in SEQ ID NO 1 can be used to prepare probes and primers for use in PCR and or NASBA techniques.

A diagnostic test kit for the detection of *Streptococcus uberis* may e.g. comprise tools to enable the reaction of bacterial nucleic acid isolated from the cows to be tested with these tools. Such tools are e.g. specific probes or (PCR-) primers, also referred to as primer fragments, based upon the nucleic add sequences according to the invention. If genetic material of *Streptococcus uberis* is present in the animal, this will e.g. specifically bind to specific PCR-primers and, e.g. after cDNA synthesis, will subsequently become amplified in PCR-reaction. The PCR-reaction product can then easily be detected in DNA gel electrophoresis.

Standard PCR-textbooks give methods for determining the length of the primers for selective PCR-reactions with *Streptococcus uberis* DNA Primer fragments with a nucleotide sequence of at least 12 nucleotides are frequently used, but primers of more than 15, more preferably 18 nucleotides are somewhat more selective. Especially primers with a length of at least 20, preferably at least 30 nucleotides are very generally applicable. PCR-techniques are extensively described in Dieffenbach & Dreksler, PCR primers, a laboratory manual. ISBN 0-87969-447-5 (1995). Nucleic acid sequences according to the invention or primers of those nucleic acid sequences having a length of at least 12, preferably 15, more preferably 18, even more preferably 20, 22, 25, 30, 35 or 40 nucleotides in that order of preference, wherein the nucleic acid sequences or parts thereof have at least 70% homology with the nucleic acid sequence as depicted in SEQ ID NO: 1 are therefore also part of the invention. Primers are understood to have a length of at least 12 nucleotides and a homology of at least 70%, more preferably 80%, 85%, 90%, 95%, 98%, 99% or even 100%, in that order of preference, with the nucleic acid sequence as depicted in SEQ ID NO: 1. Such nucleic acid sequences can be used as primer fragments in PCR-reactions in order to enhance the amount of DNA that they encode or in hybridization reactions. This allows the quick amplification or detection on blots of specific nucleotide sequences for use as a diagnostic tool for e.g. the detection of *Streptococcus uberis* as indicated above.

Another test on genetic material is based upon growth of bacterial material obtained from e.g. a swab, followed by classical DNA purification followed by classical hybridization with radioactively or color-labeled primer fragments. Colour-labelled and radioactively labeled fragments are generally called detection means. Both PCR-reactions and hybridization reactions are well-known in the art and are i.a. described in Maniatis/Sambrook (Sambrook, J. et al. Molecular cloning: a laboratory manual. ISBN 0-87969-309-6).

Thus, one embodiment of the invention relates to a diagnostic test kit for the detection of *Streptococcus uberis* nucleic acid sequences. Such a test comprises a nucleic acid sequence according to the invention or a primer fragment thereof.

A diagnostic test kit based upon the detection of antigenic material of the specific *Streptococcus uberis* 22.5 kD protein and therefore suitable for the detection of *Streptococcus uberis* infection may i.a. comprise a standard ELISA test. In one example of such a test the walls of the wells of an ELISA plate are coated with antibodies directed against the 22.5 kD protein. After incubation with the material to be tested, labeled anti-*Streptococcus uberis* antibodies are added to the wells. A color reaction then reveals the presence of antigenic material from *Streptococcus uberis*.

Therefore, still another embodiment of the present invention relates to diagnostic test kits for the detection of antigenic material of *Streptococcus uberis*. Such test kits comprise antibodies against a 22.5 kD protein or a fragment thereof according to the invention.

A diagnostic test kit based upon the detection in serum of antibodies against the 22.5 kD protein of *Streptococcus uberis* and therefore suitable for the detection of *Streptococcus uberis* infection may i.a. comprise a standard ELISA test. In such a test the walls of the wells of an ELISA plate can e.g. be coated with the 22.5 kD protein. After incubation with the material to be tested, labeled anti-22.5 kD antibodies are added to the wells. A lack of color reaction then reveals the presence of antibodies against *Streptococcus uberis*.

Therefore, still another embodiment of the present invention relates to diagnostic test kits for the detection of antibodies against *Streptococcus uberis*. Such test kits comprise the 22.5 kD *Streptococcus uberis* protein or a fragment thereof according to the invention.

The design of the immunoassay may vary. For example, the immunoassay may be based upon competition or direct reaction. Furthermore, protocols may use solid supports or may use cellular material. The detection of the antibody-antigen complex may involve the use of labeled antibodies; the labels may be, for example, enzymes, fluorescent-, chemoluminescent-, radio-active- or dye molecules.

Suitable methods for the detection of antibodies reactive with a protein according to the present invention in the sample include the enzyme-linked immunosorbent assay (ELISA), immunofluorescense test (IFT) and Western blot analysis.

The proteins or immunogenic fragments thereof according to the invention e.g. expressed as indicated above can be used to produce antibodies, which may be polyclonal, monospecific or monoclonal (or derivatives thereof). If polygonal antibodies are desired, techniques for producing and processing polyclonal sera are well-known in the art (e.g. Mayer and Walter, eds. *Immunochemical Methods in Cell and Molecular Biology*, Academic Press, London, 1987).

Monoclonal antibodies, reactive against the protein according to the invention or an immunogenic fragment thereof according to the present invention, can be prepared by immunizing inbred mice by techniques also known in the art (Kohler and Milstein, *Nature*, 256, 495-497, 1975).

EXAMPLE

Example 1

Cloning and expression of the gene encoding the 22.5 kDa S. uberis protein

The amino acid sequence of the 22.5 kDa protein according to the invention contains a hydrophobic N-terminal signal sequence of 21residues (SEQ ID 2). For expression in *E.coli* this domain was deleted and an expression construct was made in a pET-derived vector pETHis1 (ampicillin-resistanee), which was constructed using a standard pET-vector as known in the art, into which i. a. several histidines were introduced. FIG. 1 SEQ ID No: 5 gives the sequence of the relevant region comprising a T7-promoter and several histidines at the 5'-and 3'-end of the multicloning site.

The DNA fragment encoding residues 22-200 of the 22.5 kDa protein was amplified by PCR using a forward primer (CATgCCATggggCATATgTATATAACA-CATCAAAATgTAC), SEQ ID No: 3 that started at residu 22 (codon underlined) with an additional NdeI restriction site (bold italics) and a reverse primer (gCgggATCCAAATTTAgATAATAATTgTATg) SEQ ID No: 4 that contained the last 22 nucleotides of the gene (underlined), lacking the TAA stop codon but with an additional BamHI restriction site. Oligonucleotides were purchased from Gibco (BRL Life Technologies Inc., USA). This cloning strategy results in an expression product with a 6×HIS tag at the N-terminus and a 10×HIS tag at the C-terminus, which could be efficiently used for purification of the protein by means of metal affinity columns.

PCR amplification was performed using a PE GeneAmp PCR system 9700 (Perkin Elmer, Califorina, USA). The PCR mixture consisted of 20 U/ml SUPERTAQ™, 1×SUPERTAQ™(Taq polymerase isolated from $E.coli$) buffer, 80 µM (each) of dATP, dCTP, dGTP, dTTP (HT Biotechnology, Ltd., Cambridge, UK), 10 pmoles of the used primers and 1 µl of the chromosomal DNA of S. uberis as a template in a total volume of 50 µl. PCR was performed using the following program: denaturation for 2 minutes at 95° C., followed by 30 cycles consisting of 30 seconds denaturation at 95° C., 30 seconds annealing at 45° C. and 1 minute elongation at 72° C., ending with 7 minutes 72° C. and cooling down to 4° C.

The size of this PCR fragment was confirmed by agaroase gel electrophoresis and the band was excized from gel and purified using the QIAQUICK™ gel (silica eel membrane that binds DNA) extraction kit (Qiagen, Inc. CA, USA).

The PCR fragment was digested with NdeI and BamHI and cloned into the pETHIS1 vector using NdeI and BamHI restriction sites, giving the plasmid pETHis1-USP22.5. The ligation mixture was transformed into a appropriate $E. coli$ host and clones were selected and verified for the correct insertion of the gene by nucleotide sequence analysis. Cycle sequencing reactions were carried out using a PE GeneAmp PCR system 9700 (Perkin Elmer, Ca, USA). The cycle sequencing reaction mix consisted of approximately 375 ng of miniprep DNA or approximately 75 ng PCR-product (PCR primers should be removed), 8 µl BIG DYE TERMINATOR READY REACTION MIX™ (colored nucleotides and corresponding enzymes) (Perkin Elmer, Ca, USA), 2.5 pmol primer in a total volume of 20 µl. Cycle sequence reaction was performed using the following program; 25 cycles with 10 seconds 95° C., 5 seconds 50° C. and 4 minutes 60° C. and then 4° C. The unincorporated dyes were removed by the DYE EX SPIN KIT™ (dye terminator removal kit) (Qiagen, Inc. CA, USA). The nucleotide sequences were determined using an ABI 310 Automatic Sequencer. Sequence analysis was performed using sequencher version 4.0.5 (Gene Codes Corporation, Michigan, USA).

Plasmid DNA of correct pETHis1-USP22.5 clones was isolated and transformed into $Eseherichia\ coli$ host strain BL21 STAR™ (DE3) containing vector pLysS [genotype: F. ompT,hsdS$_B$ ( r$_b$-, m$_b$-), gal, dcm, me131 one shot chemically competent $E.\ coli$ bacterial strain) (DE3) pLysS (Cam$^R$)]. $E.\ coli$ strain BL21 STAR™ (DE3) containing the plasmid pLysS and pETHis1-USP22.5 was grown overnight at 30° C. or 37° C. and 200 rpm in 5 ml TERRIFIC BROTH™ (tryptone. yeast and 2glycerol culture medium) (Sambrook et al. 1989. Molecular Cloning; a laboratory manual. Cold Spring Harbor Laboratory. Cold Spring Harbor, N.Y.) with 100 µg/ml ampicillin, 25 µg/ml chioramphenicol and 5 mM MgSO$_4$.

This overnight culture was diluted 1:50 in 50 ml of the same fresh medium.

These cultures were grown under the same conditions until the OD$_{600}$ had reached 0.5, 20 measured at 600 nm on a NOVASPEC II™ spectrophotometer (Pharmacia). At this point a 100 µl sample was taken for analysis. At OD$_{600}$ of 0.5 the cultures were induced with IPTG to a final concentration of 0.1 mM and continued to grow for a subsequent 3 hours. Again, a 100 µl sample was taken for analysis. The samples were analysed on a NuPAGE™ electrophoresis System by SDS-PAGE. The gels were stained with Coomassie Brilliant Blue (CBB).

FIG. 2 shows a photograph of a CBB stained gel with a clear protein band of approximately 23 kDa in the lane of induced culture, which is absent in the control lane before IPTG induction. In conclusion it can be said that the 22.5 kDa protein of S. uberis can be efficiently expressed as a HIS-tagged protein in $E. coli$.

Metal Affinity Purification of HIS-Tagged Proteins

The bacterial pellet of 50 ml induction culture was defrozen at 37° C. for 5 minutes. The pellet was resuspended in 20 ml lysisbuffer (8M Urea, 100 mM NaCl, 50 mM NaH$_2$PO$_4$, 10 mM TrisHCl pH8.0) and incubated on room temperature for 15 minutes. A sample of the lysis mixture was saved for further analysis Add 1.5 ml of the lysis mixture to a Talon spin column (Clontech, Palo Alto, Calif., USA). The His fusion protein was allowed to bind to the resin for 5 minutes. The column was centrifuge for 2 minutes at 700×g. The eluate was saved for further analysis. The column with the bound fusion protein was washed three times with 1 ml lysisbuffer. The flow throughs of the wash step were saved for further analysis. The bound protein was eluted in 2 steps using 6 M urea and 100 mM EDTA buffer. Using this method the 22.d kDa protein could be purified from the $E.\ coli$ lysate (data not shown).

Example 2

Immunoblotting of the Expressed 22.5 kD Protein

In order to show reactivity of the $E.\ coli$ 22.5 kDa expression product, an immunoblot was done.

Purified, His-tagged 22.5 kDa protein was run on a protein gel along with S. uberis proteins. S. uberis was grown under standard conditions and then treated with mutanolysin, an emzyme that degrades the cell wall of streptococcal species. In this way, cell wall associated proteins will be released. After centrifugation these released proteins will be present in the supernatant. Both, supernatant and cell pellet were run on the protein gel.

After electrophoresis of the purified 22.5 kD protein and the S. uberis proteins, the gel was blotted onto nitrocellulose membrane and then incubated with 1:1000 diluted antiserum from a cow suffering from S. uberis mastitis. Bovine antibodies reacting with S. uberis and $E. coli$ proteins were stained with anti-bovine conjugated alkaline phophatase.

In the lane comprising the purified 22.5 kDa expression product a clear band of approximately 23 kDa was visible. In Western immunoblotting this band reacted positive with antibodies from S. uberis infected cows. (see FIG. 2 lane 6). In addition a band with a similar molecular weight was observed in lanes 3 and 5 which contained supernatant of mutanolysin treated S. uberis cells. Slight differences in molecular weight are caused by the extra HIS residues of the $E.\ coli$ expression product. This indicates that the 22.5 kDa protein is located in the cell wall or on the surface of S. uberis cells.

In conclusion, the 22.5 kD Streptococcus uberis protein according to the invention can be efficiently expressed and subsequently isolated, and immunoreacts with antiserum from *Streptococcus uberis* infected cows to a level comparable with the native 22.5 kD protein.

LEGEND TO THE FIGURES

FIG. 1. Section of the pETHIS 1 vector containing the T7 promoter and multiple cloning site with two HIS tags: 6×HIS at N-terminus and 10×HIS at C-terminus. (SEQ ID NO: 5 and SEQ ID NO:6).

FIG. 2. SDS-PAAGE gel showing expression in *E. coli* of the 22.5 kD *Streptococcus uberis* protein.

Lane 1 shows the marker proteins and their molecular weight. Lane 2, marked "before" shows a whole cell preparation before induction of expression. Lane 3, marked "after" shows a whole cell preparation after induction of expression. A clear 22.5 kD band (marked with an arrow) is seen in the lane marked "after" on the SDS-PAAGE gel.

FIG. 3. Western blot of the 22.5 kD *Streptococcus uberis* protein expressed in *E. coli*.

Lane 1: MN markers, lane 2: *S. uberis* strain 024 pellet after mutanolysin treatment, lane 3: *S. uberis* strain 024 supernatant after mutanolysin treatment, lane 4: *S. uberis* strain 629 pellet after mutanolysin treatment, lane 5: *S. uberis* strain 629 supernatant after mutanolysin treatment, lane 6: HIS-tagged 22.5 kDa protein, purified from *E. coli* cells.

The invention claimed is:

1. An isolated, cell wall associated, 22.5 kD *Streptococcus uberis* protein, said protein having the amino acid sequence comprising SEQ ID NO: 2.

2. The isolated 22.5 kD *Streptococcus uberis* protein according to claim 1, wherein said protein is encoded by the nucleic acid sequence set forth in SEQ ID NO:1.

3. An immunogenic composition comprising an isolated 22.5 kD *Streptococcus uberis* protein according to claim 1.

* * * * *